(12) United States Patent
Singh et al.

(10) Patent No.: US 7,783,093 B2
(45) Date of Patent: Aug. 24, 2010

(54) METHOD FOR LOCATING A CURVED OBJECT

(75) Inventors: Arun Singh, North Wales, PA (US); Edward Marandola, Gwynedd, PA (US); Omid Kia, North Bethesda, MD (US); Uwe Mundry, Mauldin, SC (US)

(73) Assignee: Imaging Sciences International LLC, Hatfield, PA (US)

( * ) Notice: Subject to any disclaimer, the term of this patent is extended or adjusted under 35 U.S.C. 154(b) by 1114 days.

(21) Appl. No.: 11/437,524

(22) Filed: May 20, 2006

(65) Prior Publication Data

US 2007/0014461 A1    Jan. 18, 2007

Related U.S. Application Data

(60) Provisional application No. 60/682,971, filed on May 20, 2005.

(51) Int. Cl.
    *G06K 9/00* (2006.01)
(52) U.S. Cl. ..................................................... 382/128
(58) Field of Classification Search ......... 382/128–134; 128/920–930; 250/455–465; 356/39–49; 600/407–414, 424–426
    See application file for complete search history.

(56) References Cited

U.S. PATENT DOCUMENTS

| 4,661,967 | A  | 4/1987  | Nishikawa      |
| 4,856,038 | A  | 8/1989  | Guenther et al.|
| 5,195,114 | A  | 3/1993  | Sairenji et al.|
| 5,214,686 | A  | 5/1993  | Webber         |
| 5,339,367 | A  | 8/1994  | Roth           |
| 5,511,106 | A  | 4/1996  | Doebert et al. |
| 5,677,940 | A  | 10/1997 | Suzuki et al.  |
| 5,784,429 | A  | 7/1998  | Arai           |
| 6,021,222 | A  | 2/2000  | Yamagata       |
| 6,049,584 | A  | 4/2000  | Pfeiffer       |
| 6,289,074 | B1 | 9/2001  | Arai et al.    |
| 6,493,415 | B1 | 12/2002 | Arai et al.    |
| 6,570,953 | B1 | 5/2003  | Dobert et al.  |
| 6,780,155 | B2 | 8/2004  | Li             |

(Continued)

FOREIGN PATENT DOCUMENTS

JP    4144548    5/1992

(Continued)

OTHER PUBLICATIONS

Office Action from U.S. Appl. No. 11/437,525 dated Sep. 27, 2007 (9 pages).

(Continued)

*Primary Examiner*—Samir A. Ahmed
*Assistant Examiner*—Atiba O Fitzpatrick
(74) *Attorney, Agent, or Firm*—Michael Best & Friedrich LLP

(57) ABSTRACT

In a method and apparatus for locating in a three dimensional data array an arcuate object having an axial extent, slices of data generally transverse to the axial extent of the object are selected. Rays generally radially of the arcuate object are selected within the slices. Crossing points where the rays cross the boundaries of the arcuate object are located. The position of the arcuate object is determined from the positions of the located points.

25 Claims, 4 Drawing Sheets

U.S. PATENT DOCUMENTS

| | | | |
|---|---|---|---|
| 6,798,860 | B1 | 9/2004 | Hsieh et al. |
| 6,859,555 | B1 | 2/2005 | Fang et al. |
| 7,039,156 | B2 | 5/2006 | Arai et al. |
| 7,369,691 | B2 | 5/2008 | Kondo et al. |
| 7,421,059 | B2 | 9/2008 | Suzuki et al. |
| 7,460,638 | B2 | 12/2008 | Singh et al. |
| 7,499,576 | B2 | 3/2009 | Setala |
| 2004/0066877 | A1* | 4/2004 | Arai et al. .................. 378/4 |
| 2004/0236210 | A1* | 11/2004 | Tsai et al. ............... 600/427 |

FOREIGN PATENT DOCUMENTS

| | | |
|---|---|---|
| JP | 2001061834 | 3/2001 |
| JP | 3621146 | 2/2005 |

OTHER PUBLICATIONS

U.S. Appl. No. 11/437,525 Third-Party Submission of Prior Art in Published Application mailed Oct. 3, 2007 (38 pages).

PCT/US06/19319 International Search Report and Written Opinion dated Nov. 8, 2007 (9 pages).

PCT/US6/19320 International Search Report and Written Opinion dated Feb. 11, 2008 (10 pages).

PCT/US2006/019320 International Preliminary Report on Patentability dated Mar. 6, 2008 (2 pages).

Office Action from U.S. Appl. No. 11/437,526 dated Feb. 26, 2008 (8 pages).

Office Action from U.S. Appl. No. 11/437,526 dated Sep. 22, 2008 (8 pages).

Office Action from U.S. Appl. No. 11/437,523 dated Dec. 29, 2009 (10 pages).

* cited by examiner

METHOD FOR LOCATING A CURVED OBJECT

CROSS REFERENCE TO RELATED APPLICATIONS

This application claims the benefit of U.S. Provisional Patent Application No. 60/682,971, filed May 20, 2005, which is imported herein by reference in its entirety.

This application is related to the following United States Patent Applications which are filed on even date herewith and which are incorporated herein by reference: application Ser. No. 11/437,523, filed on May 20, 2006, allowed on Jun. 24, 2010, entitled LOCATION OF ELONGATED OBJECT; application Ser. No. 11/437,525, filed on May 20, 2006, now U.S. Pat. No. 7,460,638, entitled LOCATION OF FOCAL PLANE; and application Ser. No. 11/437,526, filed on May 20, 2006, now U.S. Pat. No. 7,545,909, entitled GENERATING PANORAMIC VIEWS OF THE JAW USING A FIXED REFERENCE POINT AND CROSSING POINTS OF MULTIPLE RAYS.

BACKGROUND

The invention relates to locating a curved object in a three-dimensional array of data, and especially, but not exclusively, to locating an unevenly curved structure in a tomographic imaging dataset. The invention has particular application to locating the maxilla, the mandible, or both in a dataset of part of the head of a human or other mammal.

In certain forms of dental medicine and surgery, a "panoramic" image of the jaw is used to examine the jaw, for example, for monitoring of dental health and condition, diagnosis, and planning of prosthetic and other surgical procedures. The panoramic image of the jaw, like a panoramic photograph, depicts the jaw as if it were imaged onto an imaginary approximately cylindrical sheet with the axis of the sheet upright, and the sheet were then unrolled into a flat form. However, the human jaw is not a perfect circular arc, so the "cylindrical" shape of the imaginary sheet is not exactly circular.

A set of three-dimensional data relating to a property of an object that varies over space within the object may be obtained in various ways. For example, an x-ray image of a target may be obtained by placing the target between a source of x-rays and a detector of the x-rays. In a computed tomography (CT) system, a series of x-ray images of a target are taken with the direction from the source to the detector differently oriented relative to the target. From these images, a three-dimensional representation of the density of x-ray absorbing material in the target may be reconstructed. Other methods of generating a three-dimensional dataset are known, including magnetic resonance imaging, or may be developed hereafter.

From the three-dimensional data, a desired section or "slice" may be generated, including a curved slice. For example, a slice curving along the jaw, corresponding to a panoramic view of the jaw may be generated, provided that the position of the jaw within the three-dimensional dataset is known. It has previously been proposed to display on a visual display unit (VDU) a horizontal section through the mandible or maxilla, and for a human user to identify, for example by controlling a cursor on the VDU or by using a stylus on a touch-sensitive VDU, enough points on the mandible or maxilla for the curve of the jaw to be interpolated. However, many dentists and oral surgeons are not skilled computer operators.

There is therefore a hitherto unfulfilled need for a system by which the arc of the jaw can be accurately identified in a tomographic dataset without relying on the skill of a human operator, so that panoramic and similar images can be reliably automatically generated.

SUMMARY

According to one embodiment of the invention, there is provided a method and system for locating in a three dimensional data array an arcuate object having an axial extent. Slices of data generally transverse to the axial extent of the object are selected. Rays generally radially of the arcuate object are selected within the slices. Crossing points where the rays cross the boundaries of the arcuate object are located. The position of the arcuate object is determined from the positions of the located points.

According to a preferred embodiment of the invention, the data array is a tomographic dataset of a human head or part thereof, and the curved object is the upper or lower jaw.

By locating the mandible or maxilla in the three-dimensional tomographic dataset, and exploiting the fact that the jaw is continuous along its length and has relatively sharp boundaries, the curve of the jaw can be identified with greater reliability than is attainable by most human operators without special skills or great effort.

The invention also provides computer software arranged to generate an image in accordance with the method of the invention, and computer-readable media containing such software. The software may be written to run on an otherwise conventional computer processing tomographic data.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Reference will now be made in detail to various embodiments of the present invention, examples of which are illustrated in the accompanying drawings.

Figure 1:
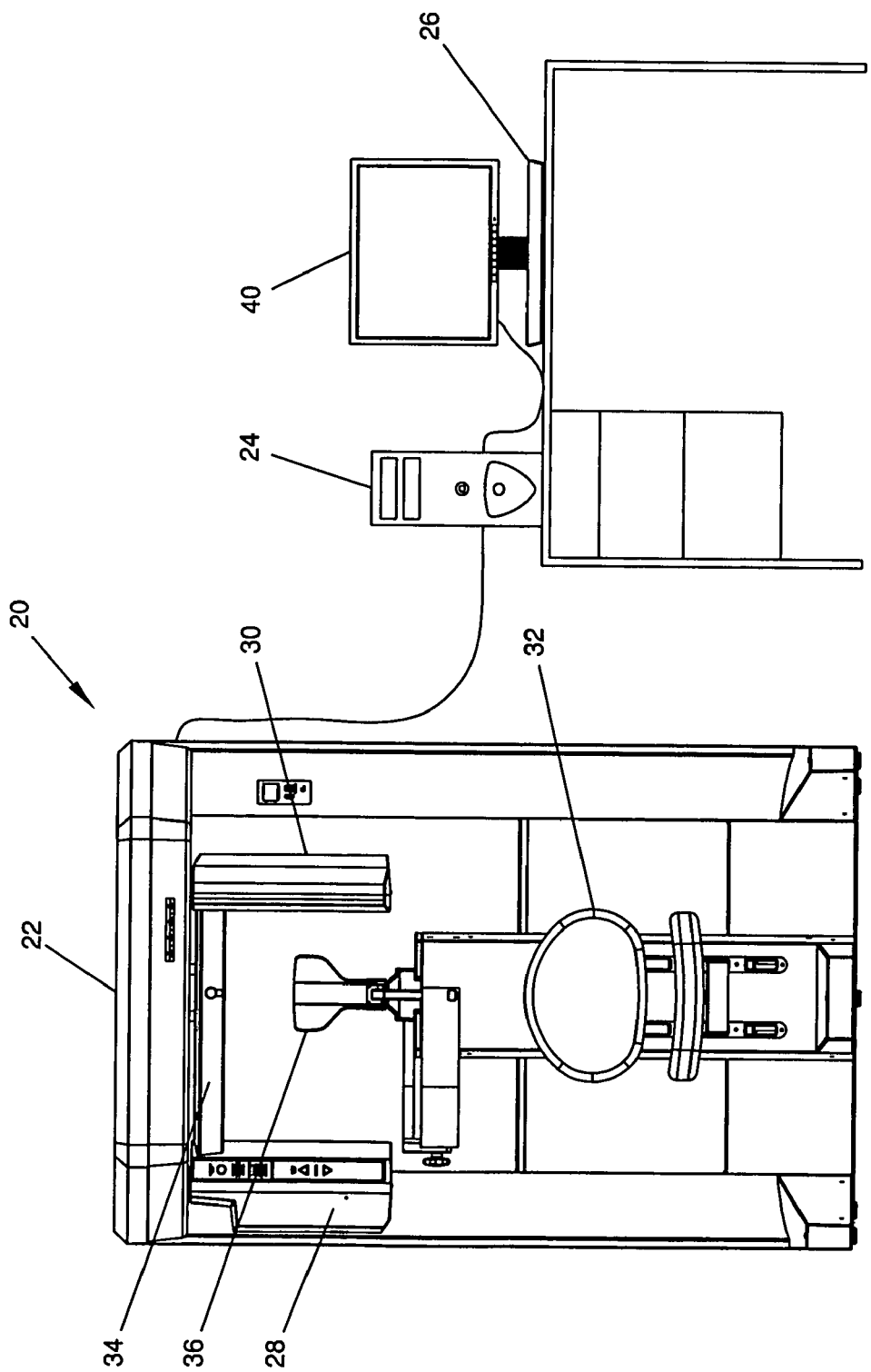
FIG. 1 is a schematic view of apparatus for generating a tomographic image.
Figure 2:
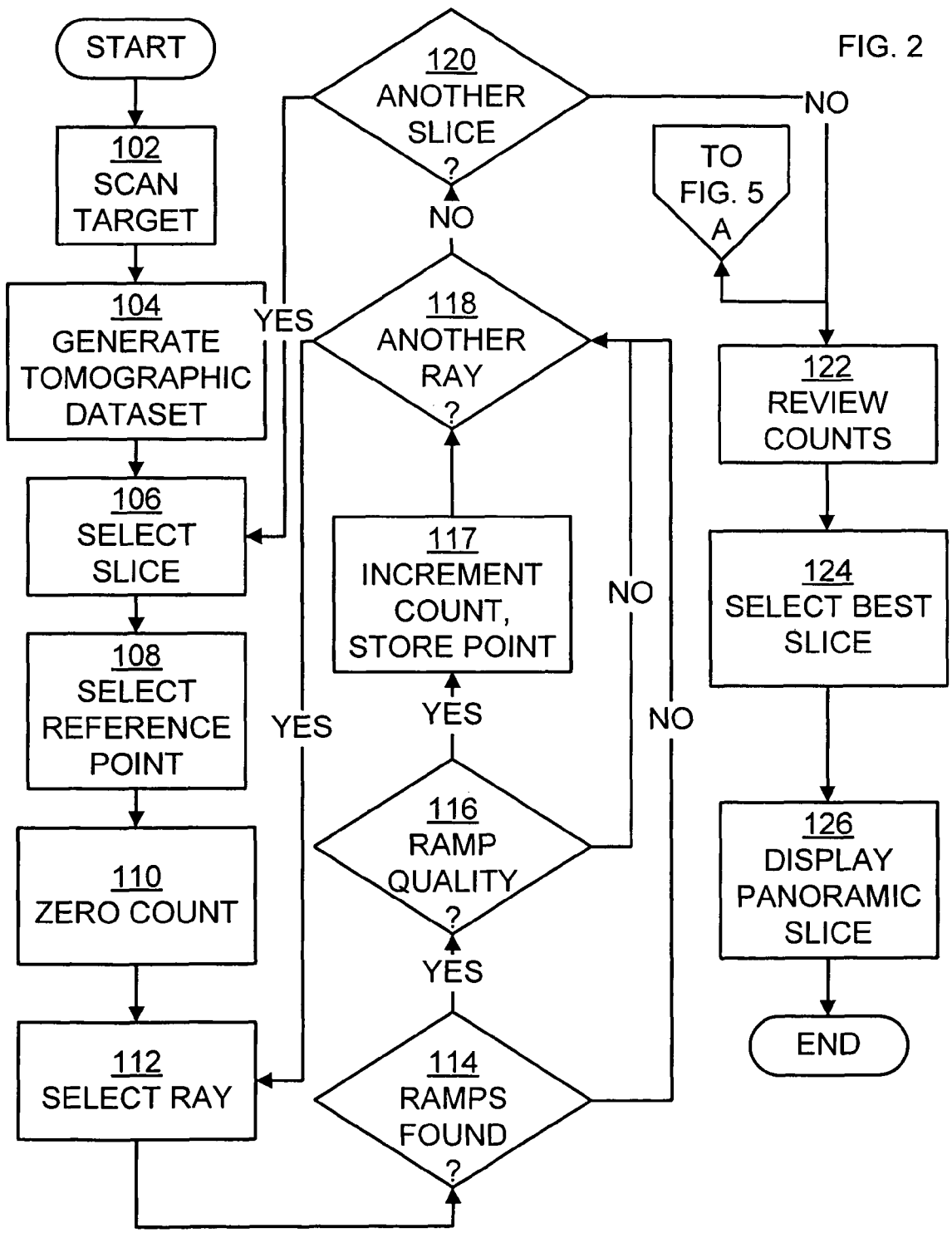
FIG. 2 is a flow chart of one embodiment of a method according to the invention.

Referring to the drawings, and initially to FIGS. 1 and 2, one form of tomographic apparatus according to an embodiment of the invention, indicated generally by the reference numeral 20, comprises a scanner 22 and a computer 24 controlled by a console 26 with a display 40. The scanner 22 comprises a source of x-rays 28, an x-ray detector 30, and a support 32 for an object to be imaged. In an embodiment, the scanner 22 is arranged to image the head, or part of the head, of a human patient (not shown), especially the jaws and teeth. The support 32 may then be a seat with a rest or restrainer 36 for the head or face (not shown) of the patient. The x-ray source 28 and detector 30 are then mounted on a rotating carrier 34 so as to circle round the position of the patient's head, while remaining aligned with one another. In step 102, the x-ray detector 30 then records a stream of x-ray shadowgrams of the patient's head from different angles. The computer 24 receives the x-ray image data from the scanner 22, and in step 104 calculates a 3-dimensional spatial distribution of x-ray density.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

Figure 4:
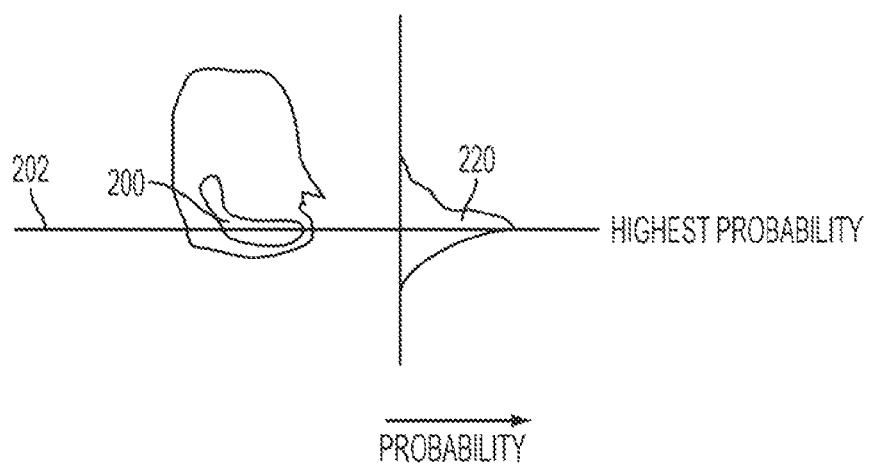
FIG. 4 is a schematic side view of a head, with a curve of probability distribution.

In step 106, an initial slice 202 through the tomographic dataset is selected. As shown in FIG. 4, the initial slice 202 is a horizontal slice, relative to the normal standing or sitting position of a human patient. For other species, the operator may select an appropriate orientation, either by positioning the patient for scanning, or by manipulation of the tomographic data. The slice may be selected by a human operator on the display 40 of the console 26, or may be selected automatically by the computer 26.

In step 108, a reference point 204 is selected. The reference point 204 is preferably on, or close to, the centerplane of the head, and approximately at the center of the dental arch. Because the dental arch is not an arc of a circle, and may not be symmetrical from side to side, very precise centering of the reference point 204 is not required, and may not be meaningfully possible. The same reference point 204 will be used in subsequent processing of other slices. Therefore, the reference point 204 may be treated as the intersection of a vertical reference line with the slice 202, and either the reference line/point 204 or the slice 202 may be selected first, or they may be selected in parallel. For subsequent slices 202, the reference point 204 is automatically selected as a point on the reference line through the reference point in the first slice.

In step 110, a probability count is set to zero.

In step 112, a ray 206 in the slice 202 extending radially away from the center point 204 through the jaw 200 is selected.

In step 114, the ray 206 is inspected to identify the points 208, 210 where the ray crosses the inner face 212 and the outer face 214 of the jaw 200. These faces 212, 214 are typically recognized as ramps in the density profile along the ray, where the density rises rapidly towards the jaw 200. The bone of the jaws typically has a markedly higher density than the surrounding soft tissue. The crossing points 208, 210 may be taken as points where the ramp crosses a selected density threshold. If the ramps are not clearly defined, for example, if the steepness or height of either or both ramp is less than a preset threshold, the ray 206 may be discarded.

If crossing points 208, 210 are identified, in step 116 the crossing points may be subjected to a quality test. For example, the ray may be discarded if the identified crossing points 208, 210 are not approximately where the jaw 200 is expected to be, are too close together or too far apart, or are out of line with the crossing points 208, 210 in neighboring rays.

If the ray passes the quality test, in step 117 the probability count is increased by one, and the position where the ray 206 crosses the jaw is recorded. In one embodiment, only the center of the jaw, which may be taken as a point 216 midway between the crossing points 208, 210, is recorded. In another embodiment, the crossing points 208, 210 are recorded instead, or in addition. If the ray 206 is discarded either at step 114 because adequate ramps are not found or at step 116 because the quality test is failed, then step 117 is bypassed.

The process then returns to step 112 to select another ray 206 in the same slice. A selected number of rays 206 evenly spaced around the arc of the jaw are selected. When it is determined in step 118 that all of the rays 206 for the slice 202 have been processed, the probability count for the slice 202 is recorded, and the process returns to step 106 to select another slice 202.

The process then repeats for each of a stack of slices 202 over a part of the tomographic dataset where, based on the normal positioning of the headrest 36 relative to the x-ray source 28 and detector 30, the jaw 200 is likely to be present. It is not usually necessary to process every voxel slice of the original dataset. Preferably, a reasonable number of slices, which may be evenly spaced or may be more closely spaced in areas of expected high probability, are processed. The initial slice 202 may be the top or bottom slice of the stack of slices, with the process working systematically down or up the stack. However, that is not necessary, and the initial slice 202 may be an arbitrary slice.

Various methods may be used to define the upper and lower bounds of the stack of slices 202 used in steps 106 to 120. A bound may be set as the upper and/or lower edge of the field of the original scan of part of the patient's head. A bound may be set manually using a vertical display of the dataset. The upper or lower edge of the mandible, or the lower edge of the maxilla, may be easily found by detecting the point where high density tissue (usually teeth or bone) abruptly disappears. Other suitable methods may also be used.

When it is determined in step 120 that all of the slices 202 have been processed, in step 122 the recorded probability counts for the different slices 202 are inspected. As shown by the curve 220 in FIG. 4, the probability counts typically vary from slice to slice, with the highest probability counts forming a peak where the jaw is most well defined and the probability value decreasing above and below the peak. Alternatively, a bimodal distribution with distinct peaks for the mandible and maxilla may be found. A high probability count indicates that few of the rays 206 were discarded, and that many of the rays have yielded points 216 that are believed correctly to indicate the position of the jaw.

In step 124, the slice 202 with the highest probability count is selected, and the center points 216 of the selected slice are selected, if the center points were calculated and recorded in step 117, or are calculated, if only the crossing points 108, 110 were recorded in step 117. If the peak of the probability curve 220 has a "plateau," where more than one neighboring slice has the identical highest probability count, any one of those slices can be chosen arbitrarily. All of those slices are likely to lie in a "good" region of the jaw. A contour line 222 representing the dental arch is then constructed through the points 216. Where a bimodal distribution is found, separate contour lines 222 may be constructed for the maxilla and the mandible.

In step 126, a synthesized panoramic slice formed from columns of voxels along the contour line 222 is then generated and presented to the user. The columns of voxels may be perpendicular to the plane of the slices 202, or may be at an angle. Where separate mandibular and maxillary contour lines 222 have been constructed, the columns of voxels may be slanted or curved to pass through both contour lines 222, giving a hybrid panoramic view that shows both the maxilla and the mandible. The synthesized panoramic slice may be one or more voxels thick. For example, the thickness of the panoramic slice may correspond to a typical value for the actual thickness of the mandible or maxilla perpendicular to the panoramic slice plane.

The thickness of the human mandible and maxilla vary, both from person to person and from point to point within the jaw. Consequently, the synthesized panoramic slice displayed in step 126 may be less than optimal because it may include too much or too little of the thickness of the jaw. If the panoramic slice is too thick, bony structure may overlay or "shade" detail in the interior of the mandible or maxilla, such as the alveolar nerve, or blur details of the root of a tooth. If the panoramic slice is too thin, bony outgrowths, protruding calcification, or displaced teeth may be missed.

Figure 5:
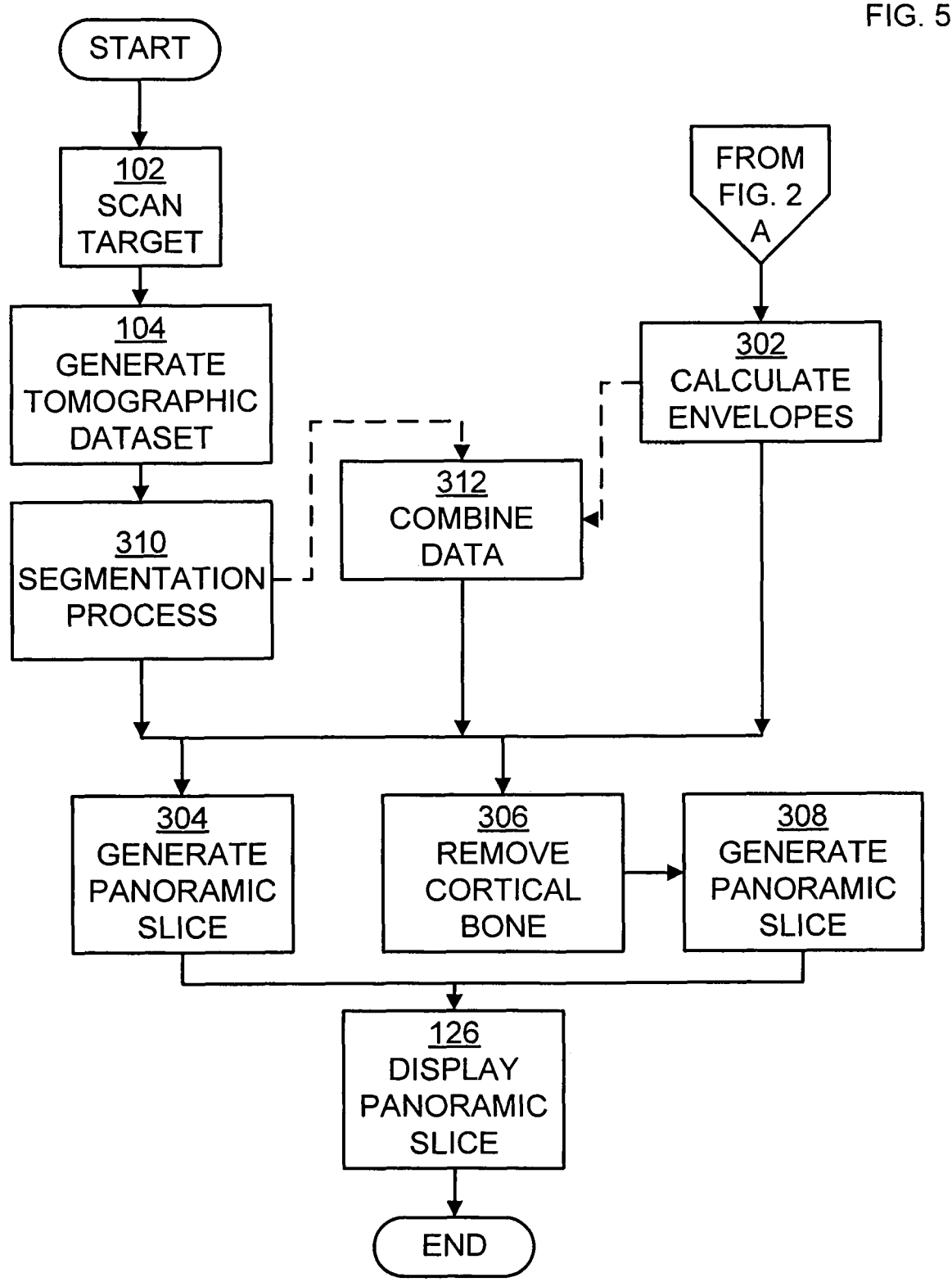
FIG. 5 is a flow chart of another embodiment of a method according to the invention.

Referring now to FIG. 5, in an alternative embodiment of a process according to the invention the crossing points 208, 210 are recorded in step 117. Then, after step 120, the process proceeds to step 302 and calculates inner and outer envelopes of the jaw 200. The inner envelope may follow the points 208 from all the accepted rays 206 in all the slices 202. The outer envelope may follow the points 210 from all the accepted rays 206 in all the slices 202. In step 304, the process then generates a panoramic slice containing the entire jawbone, except for projections too small to be reflected in the array of crossing points 208, 210.

Alternatively, if it is desired to view the internal structure of the mandible or maxilla, part of the cortical bone may be virtually "machined" away to generate a slice in which less bone is present to obscure the view. In step 306, the process may select, or get from a user, a figure for the amount of machining, for example, a "percentage of erosion." The panoramic slice is then generated in step 308, omitting a corresponding part of the cortical bone. For example, where the panoramic slice in step 304 extends from −50% to +50% of the thickness of the jaw, centered on the contour 222 at 0%, a panoramic slice with 30% erosion may extend from −35% to +35%. Other patterns of erosion or machining may be used, for example, removal of a constant thickness of bone.

In step 310, the tomographic data generated as described above with reference to steps 102, 104 in FIG. 2 may be subjected to a segmentation process known in other fields to discriminate between the targeted mandible or maxilla and other tissues. The segmentation process typically comprises of defining an initially arbitrary contour through the dataset. The contour may be a surface in the three dimensional dataset or a line in a slice 202. In an iterative process, the contour is then adjusted and assessed by some criterion for its fit to the surface of the mandible or maxilla. The criterion may test, for example, how much of the contour is in areas of high density gradient. The iterative process may lock into place parts of the contour that are on local maxima of the density gradient, while continuing to adjust other parts of the contour. Segmentation processes and suitable iterative algorithms are well known in other fields of image processing, and in the interests of conciseness the segmentation is not further discussed here.

Where the segmentation process is carried out using a surface as the contour, the final result may be equivalent to the envelope generated in step 302, and may be passed directly to steps 304 and 306. Where the segmentation process is carried out on individual slices 202, the slice contours may be stacked and an envelope interpolated similarly to step 202. Where both an envelope surface from step 302 and a segmentation surface from step 310 are available, the two surfaces may be compared in step 312 to corroborate the identification of the actual jaw surface. Alternatively, portions of the jaw may be located by the process of steps 106 to 120, and portions by segmentation, and combined in step 312 to give a full surface.

For example, a three dimensional segmentation process may be better suited to parts of the head where the bone surface is not close to vertical relative to the axis 204.

Also, the segmentation process can identify and distinguish separate bony structures in the same dataset. In FIG. 2, only one good set of points 216 is needed, so if some rays 206 inadvertently detect edges on structures other than the targeted mandible or maxilla, those rays, and if necessary entire slices 202, can be discarded as aberrant. However in FIG. 5, it is desirable to have as many correctly identified points 208, 210 as possible, or as nearly a continuous surface found by segmentation as possible, so using the segmentation method to separate out other bony structures and reduce the amount of data discarded as ambiguous or unclear can be beneficial. Step 114 may then accept multiple crossing points 208, 210, and a later step, for example, step 116, may use segmentation or other discrimination process to select the crossing point 208 or 210 that belongs to the targeted mandible or maxilla.

Various modifications and variations can be made in the present invention without departing from the spirit or scope of the invention. For example, the order of the steps may be changed. In FIG. 2, more than one, or all, of the rays 206 may be processed to identify the crossing points 208, 210 before the first rays 206 are subjected to the quality test in step 116. In particular, the test for out-of-line points cannot usually be completed until points from neighboring rays 206 are available for comparison. Alternatively, or in addition, rays in neighboring slices 202 may be used for comparison.

In a further alternative, in step 124 two or more slices 202 with high probability counts may be combined. An average of the positions of the contour lines 222, which may be weighted according to the probability counts of the respective slices 202, may be used, or a consensus curve may be determined by combining only contour lines 222 that agree within a narrow tolerance.

As described with reference to FIG. 2, steps 106 through 120 repeat for each of a stack of slices 202 over the height of the jaw 200. Alternatively, the process may start with a slice 202 near the expected location of the probability peak of curve 220. The process may then proceed both up and down, with the probability count being reviewed as each slice is completed. Step 120 may then terminate the process in each direction when the probability count drops below a threshold, which may be either absolute or relative to the highest detected count, so that the process is confident that the peak is within the part of the stack of slices 202 that has been processed.

Where steps 114 and 116 find only one clear crossing point 208 or 210, step 302 may use that one point, although in step 124, a single crossing point 208 or 210 may be unhelpful for constructing the center point 216.

For example, FIG. 1 shows that the computer 24 on which the processes of FIGS. 2 and 5 is running is connected to the scanner 22. A single computer 24 may both control the scanner 22 and run the processes of FIGS. 2 and 5. Alternatively, part or all of the process of FIG. 2 and/or FIG. 5 may be carried out on a separate computer. The data from the scanner 22 may be transferred from computer to computer in a convenient format, for example the DICOM format, at a convenient stage of the process. The data may, for example, be transferred directly from computer to computer or may, for example, be uploaded to and downloaded from a storage server.

For example, in the processes described above, it is assumed that the number of rays is equal in all slices, and the rays are uniformly spaced. The number of rays may vary from slice to slice, provided that an appropriate allowance is made at steps 122 and 124. The rays may be more closely spaced at parts of the jaw where a small radius of curvature and/or a rapid change in curvature is expected. In the process of FIG. 2, for example, the selected slice may have a few discarded rays, and the ray spacing is desirably sufficiently close that a correct contour 222 can be interpolated with a desired degree of accuracy across at least one missing point 216.

For example, it is not necessary for the reference points 204 of the different slices 202 all to lie on a straight line. However, using consistent reference points 204 typically gives more consistent, and thus more comparable results, and may give a more accurate decision in step 124. In step 302, using consistent reference points 204 gives a more consistent relationship between the arrays of crossing points 208 and 210 and may make the generation of the envelopes computationally simpler. In addition, using a vertical line of points 204 is usually the simplest approach.

Figure 3:
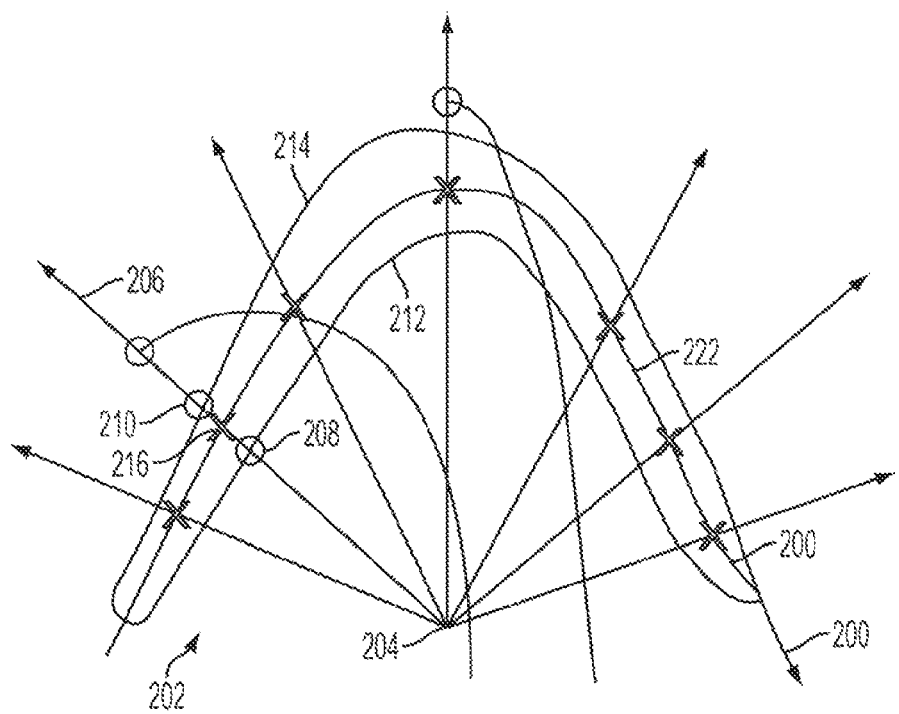
FIG. 3 is a schematic plan view of a jaw.

Although distinct embodiments have been described, features of different embodiments may be combined. For example, the contour 222 shown in FIG. 3 may be obtained as a middle line between inner and outer contours obtained by the segmentation process of step 310.

Thus, it is intended that the present invention cover modifications and variations of this invention provided they come within the scope of the appended claims and their equivalents.

What is claimed is:

1. A method of locating in a three dimensional data array an arcuate object having an axial extent, the method comprising:
    selecting slices of data from the three dimensional data array, where the slices are generally transverse to the axial extent of the object;
    selecting rays generally radially of the arcuate object within the slices;
    locating crossing points where the rays cross the boundaries of the arcuate object; and
    determining the position of the arcuate object from the positions of the located points,
    wherein locating crossing points further comprises detecting a first crossing point where the ray enters the arcuate object and a second crossing point where the ray leaves the arcuate object, and wherein determining the position of the arcuate object comprises determining a midpoint between the first and second crossing points and determining a contour through the midpoints.

2. A method according to claim 1, further comprising selecting at least one slice having a relatively high count of located crossing points, and wherein determining the position of the arcuate object comprises determining from the positions of the located points in the at least one slice.

3. A method according to claim 2, further comprising selecting a certain number of rays in each selected slice, and counting the number of located crossing points.

4. A method according to claim 2, further comprising discarding crossing points that are inconsistent with crossing points detected in neighboring rays.

5. A method according to claim 1, further comprising selecting a slice of data centered on the contour through the midpoints.

6. A method according to claim 1, further comprising generating surfaces through detected crossing points on an inside and an outside surface of the arcuate object.

7. A method according to claim 6, further comprising selecting a slice of data comprising the data occupying a space between the inner and outer generated surfaces.

8. A method according to claim 1, wherein the arcuate object is an anatomical feature, and wherein the data array comprises tomographic data of at least part of a human or animal.

9. A method according to claim 8, wherein the data array comprises tomographic data of at least one of a mandible and a maxilla.

10. A computer program, stored on a non-transitory computer-readable medium, for
    locating an arcuate object having an axial extent in a three dimensional data array, comprising
    instructions to cause a computer to:
        select slices of data generally transverse to the axial extent of the object;
        select rays generally radially of the arcuate object within the slices;
        locate crossing points where the rays cross the boundaries of the arcuate object;
        determine the position of the arcuate object from the positions of the located points; and
        detect a first crossing point where the ray enters the arcuate object and a second crossing
    point where the ray leaves the arcuate object, to determine a midpoint between the first and
    second crossing points, and to determine a curve through the midpoints.

11. A computer program stored on a non-transitory computer-readable medium according to claim 10, further comprising instructions to cause the computer to select at least one slice having a relatively high count of located crossing points, and to determine the position of the arcuate object from the positions of the located points in the at least one slice.

12. A computer program stored on a non-transitory computer-readable medium according to claim 10, further comprising instructions to cause the computer to select a certain number of rays in each selected slice, and count the number of located crossing points in each selected slice.

13. A computer program stored on a non-transitory computer-readable medium according to claim 10, further comprising instructions to cause the computer to discard crossing points that are inconsistent with crossing points detected in neighboring rays.

14. A computer program stored on a non-transitory computer-readable medium according to claim 10, further comprising instructions to cause the computer to generate surfaces through detected crossing points on an inside and an outside surface of the arcuate object.

15. A computer program stored on a non-transitory computer-readable medium according to claim 14, further comprising instructions to cause the computer to select a slice of data comprising the data occupying a space between the inner and outer generated surfaces.

16. A machine-readable medium storing a non-transitory computer program according to claim 10.

17. Apparatus comprising a computer programmed with a program according to claim 10.

18. Apparatus according to claim 17, further comprising a tomographic scanner, and arranged to generate the three dimensional data array from data generated by the scanner so as to represent an object scanned by the scanner.

19. A method of locating in a three dimensional data array an arcuate object having an axial extent, the method comprising:
    selecting slices of data from the three dimensional data array, where the slices are generally transverse to the axial extent of the object;

selecting rays generally radially of the arcuate object within the slices;

locating crossing points where the rays cross the boundaries of the arcuate object, wherein locating crossing points further comprises detecting a first crossing point where the ray enters the arcuate object and a second crossing point where the ray leaves the arcuate object, and wherein determining the position of the arcuate object comprises determining a midpoint between the first and second crossing points and determining a contour through the midpoints;

determining the position of the arcuate object from the positions of the located points; and generating surfaces through detected crossing points on an inside and an outside surface of the arcuate object.

20. A method according to claim 19, further comprising selecting at least one slice having a relatively high count of located crossing points, and wherein determining the position of the arcuate object comprises determining from the positions of the located points in the at least one slice.

21. A method according to claim 20, further comprising selecting a certain number of rays in each selected slice, and counting the number of located crossing points.

22. A method according to claim 20, further comprising discarding crossing points that are inconsistent with crossing points detected in neighboring rays.

23. A method according to claim 19, further comprising selecting a slice of data comprising the data occupying a space between the inner and outer generated surfaces.

24. A method according to claim 19, wherein the arcuate object is an anatomical feature, and wherein the data array comprises tomographic data of at least part of a human or animal.

25. A method according to claim 24, wherein the data array comprises tomographic data of at least one of a mandible and a maxilla.

* * * * *